United States Patent
Horiuchi et al.

(10) Patent No.: US 6,897,046 B2
(45) Date of Patent: May 24, 2005

(54) PROCESS OF PREPARING BIOLOGICALLY ACTIVE SUBSTANCE

(75) Inventors: Isao Horiuchi, Higashi-Yatsushiro-gun (JP); Takeru Suyama, Minami-Tsuru-gun (JP); Tsunehisa Morio, Tokyo (JP)

(73) Assignee: Japan Applied Microbiology Research Institute Ltd., Yamanashi-ken (JP)

( * ) Notice: Subject to any disclaimer, the term of this patent is extended or adjusted under 35 U.S.C. 154(b) by 201 days.

(21) Appl. No.: 10/232,830

(22) Filed: Sep. 3, 2002

(65) Prior Publication Data

US 2003/0064484 A1 Apr. 3, 2003

Related U.S. Application Data

(63) Continuation-in-part of application No. 09/478,438, filed on Jan. 6, 2000, now Pat. No. 6,465,218, which is a continuation-in-part of application No. 09/056,853, filed on Apr. 8, 1998, now abandoned.

(30) Foreign Application Priority Data

Apr. 8, 1997 (JP) .............................................. 9-089378

(51) Int. Cl.$^7$ .......................... C12P 19/00; C12P 19/04; D21C 3/00
(52) U.S. Cl. .......................... 435/72; 435/101; 435/274; 435/278
(58) Field of Search .......................... 435/72, 101, 274, 435/278, 172.3

(56) References Cited

U.S. PATENT DOCUMENTS 3,880,742 A 4/1975 James et al.
6,465,218 B1 * 10/2002 Horiuchi et al.

OTHER PUBLICATIONS

Gattinger et al, "Enzymatic Saccharification of Canola Meal," *J. Chem. Tech. Biotechnol.*, 49:155–164 (1990).

* cited by examiner

*Primary Examiner*—Michele C. Flood
(74) *Attorney, Agent, or Firm*—Browdy and Neimark, P.L.L.C.

(57) ABSTRACT

The yield of active polysaccharides contained in *Agaricus blazei*, such as β-glucan, can be improved, by decomposing and treating the mycelium or fruit body of *Agaricus blazei* or a liquid waste of the culture of the mycelium with an enzymatic agent principally comprising hemicellulase.

By increasing the concentrations of the active polysaccharides, furthermore, the digestion and absorption of the biologically active substance of the present invention after the incorporation thereof into bodies is prominently elevated, so that the active substance can exert excellent immune activation effect on cancers and other adult diseases.

15 Claims, 5 Drawing Sheets

PROCESS OF PREPARING BIOLOGICALLY ACTIVE SUBSTANCE

This is a continuation-in-part of parent application Ser. No. 09/478,438, filed Jan. 6, 2000, now U.S. Pat. No. 6,465,218 which in turn is a continuation-in-part of application Ser. No. 09/056,853, filed Apr. 8, 1998 abandoned.

BACKGROUND OF THE INVENTION

1. Field of the Invention

The present invention relates to a biologically active substance recovered from the mycelium and fruit body of *Agaricus blazei*; and a process of preparing the biologically active substance.

2. Description of the Prior Art

*Agaricus blazei* is a mushroom of Basidiommycetes from Brazil. It has been known that the mushroom is very effective for treating cancer and other adult diseases. In recent years, an artificial method for cultivating the mushroom has been developed, but because of the difficulty in the cultivation, currently, the supply is far lower than the growing demand.

Alternatively, research has been conducted regarding *Agaricus blazei* from a medical and nutritional standpoint, reporting that the principally effective component of the mushroom is β-glucan, one of the polysaccharides. β-glucan has such high immune activation potency that the glucan can activate immune cells (for example, natural killer cells) thereby attacking cancer cells and killing the cells. It has been known that β-glucan is also present in mushrooms other than *Agaricus blazei* such as shiitake (*Cortinellus shiitake*) and *maitake*.

Renntinan extracted from shiitake as well as crestin extracted from kawaratake have been formulated as anti-cancer agents. Some current research has suggested that *Agaricus blazei* is a mushroom with the highest anti-cancer action.

Methods for extracting effective polysaccharides such as β-glucan from *Agaricus blazei* have been proposed conventionally (for example, Japanese Patent Disclosure No. 1-67195). Because the content of β-glucan is very low in *Agaricus blazei*, however, a great amount of *Agaricus blazei* is required, to recover a given amount of the extract. Furthermore, Japanese Patent Disclosure No. 5-268905 describes a method for extracting extractable components from whole *Agaricus blazei* by using an enzymatic agent. In this method, an extract solution with flavor like *matsutake* (*Armillaria matsutake*) can be recovered, through the action of enzymatic agents containing endo-1,4-β-glucanase, xylanase and endo-1,3-β-glucanase on *Agaricus blazei*.

By the method for extracting such extractable components, however, β-glucan contained in the whole *Agaricus blazei* or β-glucan recovered during the intermediate stage of treating the mushroom may further be decomposed to generate cellobiose and glucose, because the enzymatic agent containing β-glucanase is utilized by the method.

SUMMARY OF THE INVENTION

It is an object of the present invention to recover a biologically active substance containing greater amounts of effective polysaccharides such as β-glucan from the mycelium fruit body of *Agaricus blazei* or the liquid waste derived from the culture of the mycelium. By utilizing hemicellulase in an enzymatic agent, in particular, an active polysaccharide containing a great amount of β-glucan is recovered through the decomposition of hemicellulose as a structural sugar of *Agaricus blazei*, so that the yield of β-glucan from *Agaricus blazei* can be improved.

So as to overcome the problems described above, the biologically active substance of the present invention characteristically contains a great amount of β-glucan produced by decomposing and treating the mycelium or fruit body of *Agaricus blazei* or a liquid waste from the culture of the mycelium with an enzymatic agent principally comprising hemicellulase.

The process of preparing the biologically active substance in accordance with the present invention comprises decomposing or treating the mycelium or fruit body of *Agaricus blazei* or a liquid waste from the culture of the mycelium with an enzymatic agent principally comprising hemicellulase.

The biologically active substance produced in accordance with the present invention contains a great amount of active low-molecular polysaccharides such as β-D-glucan, and additionally contains effective ingredients such as nucleic acid other than the polysaccharides. The molecular weights of the active Polysaccharides are about 2,000,000 to 500,000. By preparing the substance from such low molecular weight substances, the digestion and absorption thereof in the body are enhanced, so that the immune activation effect can be exerted.

The mycelium of *Agaricus blazei* can be prepared in liquid culture or solid culture. Because the liquid waste of the culture of the mycelium of *Agaricus blazei* other than the fruit body thereof contains β-glucan, such biologically active substance can be recovered from the liquid waste.

The enzymatic agent to be used in accordance with the present invention principally comprises hemicellulase. As the hemicellulase of the present invention, use is made of enzyme groups (for example, mannase, arabinosidase, xylobiase, etc.) recovered from the culture of *Tricoderma biride* JAM 4033, *Tricoderma haldianum* JAM4031, *Aspergillus temari* JAM 4007 and *Aspergillus niger* JAM 4012; and general enzymatic agents commercially available (for example, hemicellulase manufactured by sigma, Co.). hemicelluase may be used singly but may also be used after hemicellulase is mixed with pectinase, whereby the step-wise/reaction of the enzyme treatment can be conducted in a smooth manner.

Figure 1:
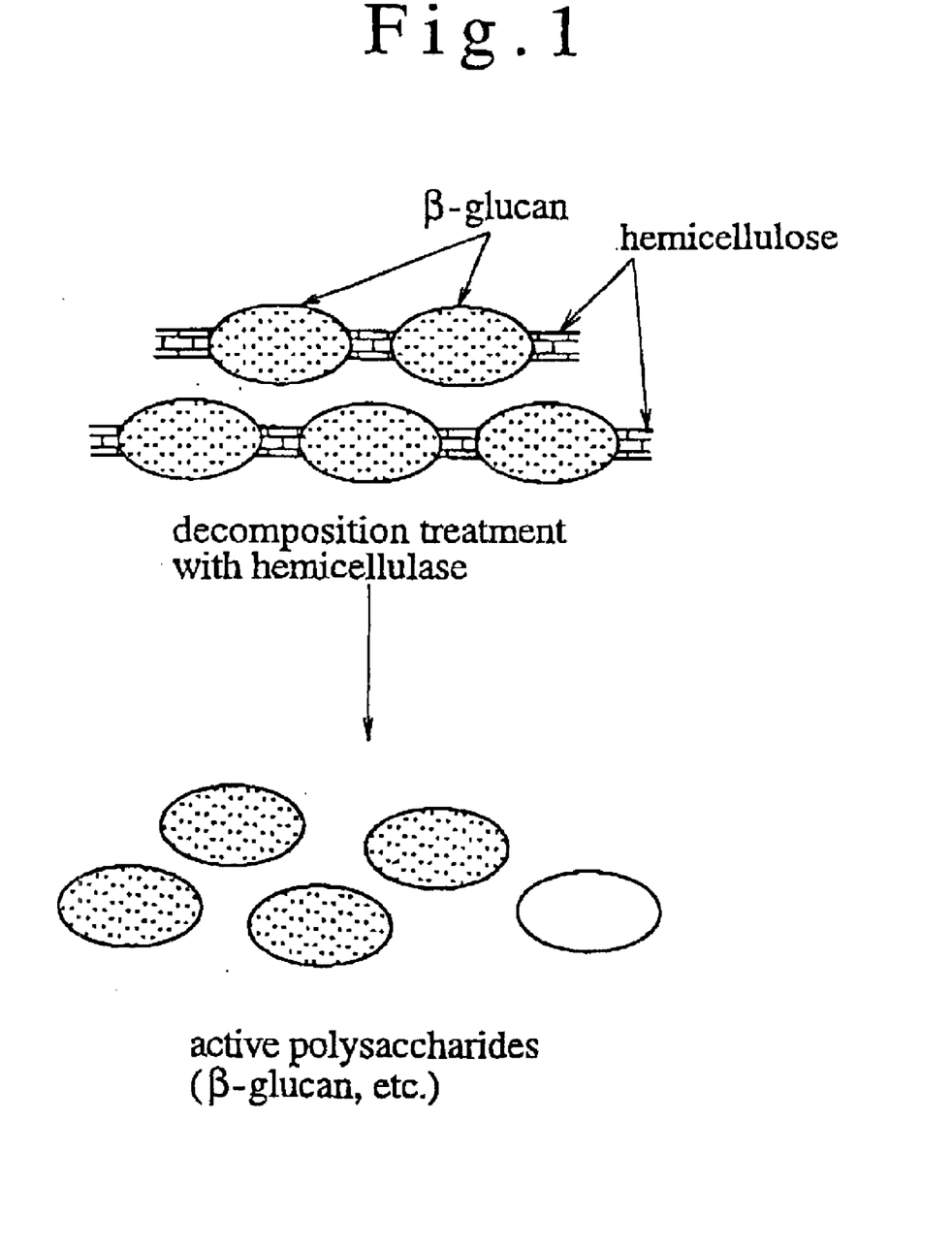
FIG. 1 is a schematic view depicting the process of preparing the biologically active substance of the present invention through decomposition.

The preparation process of β-glucan comprising enzymatically treating the mycelium thereby decomposing the mycelium is described in the schematic view of FIG. 1. Xylan, mannan and arabinan and the like in addition to β-glucan are bound together to compose a long-chain fiber in the mycelium.

By reacting an enzymatic agent in a mixture with hemi-cellulase or pectinase with the mycelium, hemicellulase is hydrolyzed in a step-wise manner, whereby the bonded chains therein are cut to prepare high-molecular polysaccharides, which are then converted to the active polysaccharide (β-D-glucan).

The ratio of the enzymatic agent added to the mycelium is 0.01 to 0.5% by weight, preferably about 0.1% by weight. The enzymatic solution for the treatment is at pH 3.0 to 8.5, preferably about pH 4.5. The temperature for the enzymatic treatment is 25 to 60° C., preferably about 45° C. Furthermore, the duration for the enzymatic treatment is 20 to 120 minutes, preferably about 60 minutes.

Just when the reaction by enzymatic treatment progresses at some extent, the solution for the treatment is heated to terminate the enzyme reaction. The enzyme is generally inactivated by heating at 80 to 100° C. for about 10 minutes. Through the termination of the enzyme reaction, the raw material of the active polysaccharide containing a greater amount of β-glucan derived from *Agaricus blazei* is produced. By condensing and drying the material, the biologically active substance of the present invention is recovered. The drying process preferably comprises freeze-drying, but may possibly comprise spray drying because the effective ingredient is relatively resistant to heat. The biologically active substance of the present invention contains α-glucan, β-galactoglucan, proteinous glucan and the like, in addition to the principal component β-glucan.

As has been described above, the mycelium or fruit body of *Agaricus blazei* or a liquid waste of the culture of the mycelium is decomposed and treated with the enzymatic agent principally comprising hemicellulase, to improve the yield of the active polysaccharide containing a greater amount of β-glucan because the concentration of the active polysaccharide can be increased. Furthermore, the digestion and absorption of the biologically active substance of the present invention after the incorporation thereof into bodies is prominently elevated, so that the active substance can exert excellent immune activation effect together with the accelerated effect on cancers and other adult diseases.

The present invention will now be described in more detail, with referente to attached drawings.

DESCRIPTION OF THE PREFERRED EMBODIMENTS

With reference to tables and the attached figures, the process of culturing the mycelium from *Agaricus blazei* will now be described below, together with examples of the enzymatic treatment of the resulting matter.

The mycelium of *Agaricus blazei* can be recovered by solid culturing or liquid culturing. The fruit body of *Agaricus blazei* can be recovered by the cultivation process previously filed by the present inventors (Japanese Patent Disclosure 9-154401). The process of preparing the mycelium of *Agaricus blazei* solid culturing comprises sterilizing, for example, a solid culture medium principally comprising malt grain or an MYA culture medium (2% malt extract, 1% yeast extract, 2% agar), inoculating the seed of *Agaricus blazei* on the medium by aseptic procedures and culturing the *Agaricus blazei* at 25° C. for 30 days.

The process of preparing the mycelium of *Agaricus blazei* by liquid culturing includes a process in an SMY culture medium. A composition example of the SYM culture medium is shown in Table 1. As the initial bacterium, use is made of a bacterial strain separated from *Agaricus blazei*. The initial bacterium is preliminarily stored in slants or stored under freezing. The strain under storage is subcultured in slants and the like, which is then transferred to liquid culture. Generally, a liquid culture medium of 100 ml is placed in a 500-ml Erlenmeyer flask, for agitation culture at 25° C. The culturing is complete in two weeks. The resulting mycelium comprises countless spheres, which the liquid phase is totally clear. Depending on the amount required, the sole should be modified. The bacterium may satisfactorily be cultured in a large tank.

TABLE 1

Composition example of SYM culture medium of Agaricus blazei mycelium

| Glucose | 2% |
|---|---|
| malt extract | 2% |
| yeast extract | 2% |
| pH | 2% |

TABLE 2

Examples of culturing conditions of Agaricus blazei mycelium

| For jar fermentorsf 25° culturing temperature; aeration volume; 1: 1 (v/v) culturing duration;. 3 weeks. |
|---|

The resulting mycelium is separated from the culture broth, whereby the mycelium is recovered. The separation process comprises mesh filtration and centrifugation. The recovered mycelium is crudely ground. because the following enzymatic reaction progresses readily in such ground mycelum.

The recovered mycelium is subjected to enzymatic treatment with an enzymatic agent principally containing hemicellulase, which is the most characteristic process in the present invention. Hemicellulase is used singly or is used in combination with pectinase preliminarily mixed into hemicellulase. The most suitable conditions for the enzymatic reaction should be selected, and one example thereof is shown in Table 3. The reaction time is generally about 1 hour.

TABLE 3

Conditions for enzymatic reaction of Agaricus blazei myceliun

| enzyme to be used; hemicellulase:pectinase = 2:1 |
|---|
| PH; 4.5 |
| Temperature; 45° |
| reaction time; 1 hour |
| concentration of enzyme solution; 0.1% |
| enzyme solution:mycelium (v/v); 2:1. |

The enzyme reaction is terminated, once the reaction progresses to some degree. The enzyme is generally inactivated by elevating the temperature to 70° C. Through the termination of the enzymatic reaction, the raw material of the active polysaccharide is recovered from *Agaricus blazei*. Because enzyme reactions due to other enzymes except hemicellulase may progress or because the raw material may possibly be putrefied by other microorganisms, however, the raw material is condensed and dried after the enzymatic treatment, to recover a sample. The drying process preferably comprises freeze-drying. Because the effective ingredient is relatively resistant thermally, however, spray drying is also satisfactory.

Instead of the elevation of the reaction temperature, the enzymatic decomposition may also be terminated by pH adjustment of the reaction liquid to inactivate the enzymatic agent. According to the present invention, the pH of the reaction liquid is adjusted to about 4.5 during the decomposition, but for terminating the reaction, the pH may be adjusted to not lower than 6.5, preferably to 7.0–7.5, to thereby inactivate the enzymatic agent.

More preferably, this pH adjustment may be combined with the temperature elevation of the reaction liquid. When the enzymatic agent is to be inactivated only by the temperature elevation of the reaction liquid without the pH adjustment, the temperature of about 45° C. during the decomposition must be elevated to as high as 80–100° C. On the other hand, when the pH of the reaction liquid is adjusted to fall within the above-mentioned range, the enzymatic agent may effectively be inactivated at not lower than 60° C., preferably 60–85° C., more preferably 70–85° C.

Figure 5:
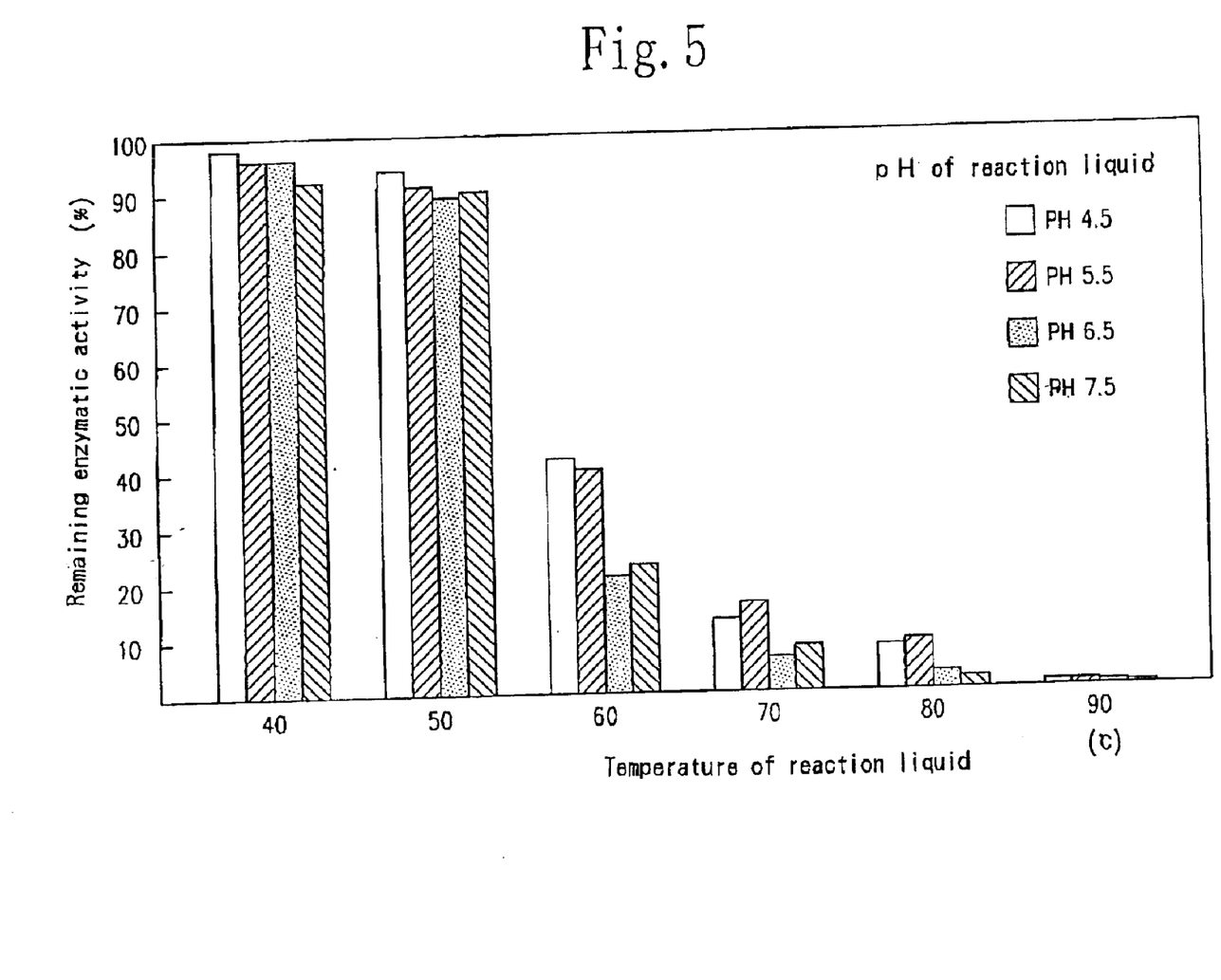
FIG. 5 shows the remaining enzymatic activity with respect to pH and temperature of the reaction liquid.

FIG. 5 shows the remaining enzymatic activity with respect to pH and temperature of the reaction liquid. This graph indicates that the remaining enzymatic activity drops at the reaction liquid temperatures of 60° C. or higher when the pH of the reaction liquids is adjusted to 6.5 or 7.5.

A process of enzymatically treating the fruit body of *Agaricus blazei* will now be described below. Because these fruit bodies belong to mycella, the process fundamentally follows the enzymatic treatment process of the mycelium as described above, with no requirement of any specific treatment process. The fruit body may be fresh or may be dry. To the fresh fruit body is added a 2-fold volume of water, and the resulting mixture is ground as it is, for subsequent enzymatic treatment. The dry fruit body is immersed in a 2-fold volume (W/W) of water for about 10 minutes, followed by grinding by means of a mixer. The resulting solution is enzymatically treated. The enzyme solution is adjusted to a final concentration of 0.1%.

The inventors executed a quantification of the β-glucan.

In this quantification, the weight of the β-glucan included in the mycelium body of the *Agaricus blazei* was quantified between one moment before the mycelium body was subjected to enzymatic treatment with an enzymatic agent principally containing hemicellulase, and the other moment after that mycelium body was subjected to the enzymatic treatment.

Also, the weight of the β-glucan included in the fruit body of the *Agaricus blazei* was quantified between one moment before the fruit body was subjected to enzymatic treatment with an enzymatic agent principally containing hemicellulase, and the other moment after that fruit body was subjected to the enzymatic treatment. The quantification process includes the steps of measuring the weight of each sample of the mycelium body and the fruit body of the *Agaricus blazei*, obtaining a filtered liquid for measurement by deposition filtrating the β-glucan and thereafter hydrolyzing it, further, the weight of glucose in the filtered liquid was quantified by glucose-oxidase method, and then the weight of the β-glucan was calculated from the following formula.

β-glucan (g/100 g)=glucose(g/100 g)×0.9

The results are shown in Table 4.

TABLE 4

| Sample | Weight of β-glucan before enzymatic treatment (g/100 g) | Weight of β-glucan After enzymatic treatment (g/100 g) |
|---|---|---|
| Mycelium body | 16~18 | Max 54 |
| Fruit body | 8~10 | Max 35 |

The results of clinical cases treated with the sample are shown below.

Clinical Case 1

Figure 2:
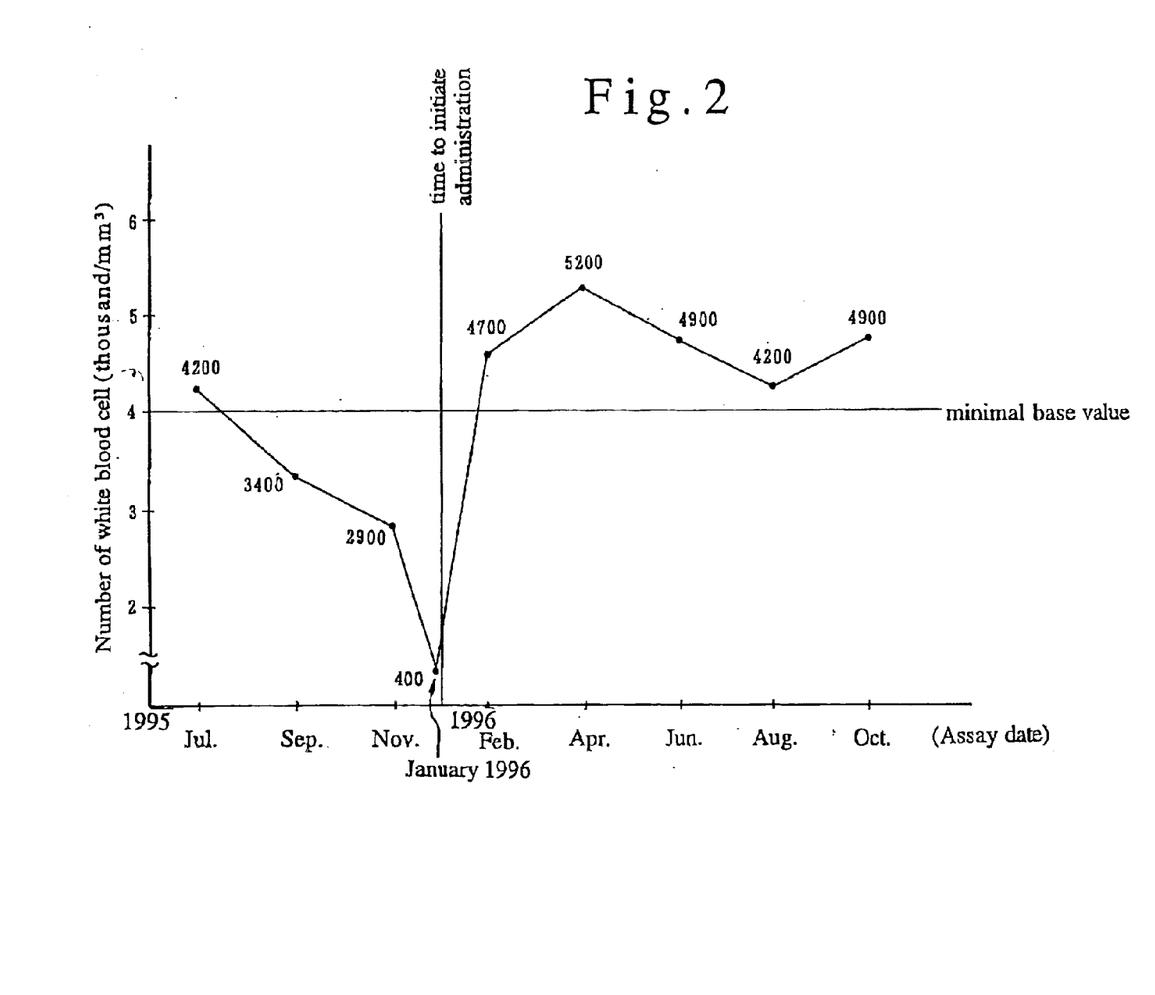
FIG. 2 shows graphs depicting the increase in white blood cells when the biologically active substance of the present invention is used.

A female (20 years old) in Hokkaido, Japan was diagnosed as having uterine cancer. It was observed at a hematological test in Jul. 24, 1995 that blood components (red blood cells, blood pigment, hematocrit, LYM, etc.) were decreased. Thereafter in Sep. 20, 1995, a decrease of white blood cells (decreased from 4200 to 3400) was observed. The number was 2900 in Nov. 13, 1995, and was subsequently decreased to 400 in the middle of January, 1996, while the increase of MCV was observed. Immediately thereafter, the biologically active substance of the present invention was administered to the patient. At a hematological test in February, 1996, the number of white blood cells was almost normal; at a subsequent test, the normal value was maintained. The change of the white cell number is shown in FIG. 2.

Clinical Case 2

At a hematological test in Feb. 27, 1996, the neutral fat and ALT in a female (age 51) in Tokyo, Japan were above the normal values. Immediately thereafter, the Patient was given the biologically active substance of the present invention. About one month later, the results of the laboratory tests were dramatically improved. On June 15, thereafter, their values were improved to almost normal. The results are show in Table 5.

TABLE 5

| Laboratory | Assay values | | | |
|---|---|---|---|---|
| Test items | H8. 2/27 | H8. 3/28 | H8. 6/15 | Base values |
| Neutral fat | 198 | 119 | 77 | 50~150 (mg/dl) |
| ALT | 62 | 57 | 41 | 5~45 (IU/L) |

Clinical Case 3

At a hematological test of a male (age 54) in Yamnanashi Prefecture, Japan, overall values were poor (for example, neutral fat of 950; hemoglobin AIC of 9.5; and blood sugar value of 233) in Jun. 1, 1994. He was administered the biologically active substance of the present invention, starting in May, 1996. At a hematological test, in Jul. 5, 1996, the values were improved. At a hematological test in Dec. 17, 1996, the values were improved to normal values. The results are shown in Table 6.

TABLE 6

| Laboratory | Assay values | | | |
|---|---|---|---|---|
| Test items | H5. 7/1 | H8. 7/5 | H8. 12/7 | Base values |
| Neutral fat | 950 | 505 | 175 | 50~150 (mg/dl) |
| Hemoglobin AIC | 9.5 | 9.1 | 7.4 | 4.3~5.8 (%) |
| Blood sugar value | 233 | 195 | 187 | 60~110 (mg/dl) |

Clinical Case 4

A female of age 45 and with hepatic cancer was administered into hospital in Jan. 3, 1997. In combination with anti-cancer agents, the biologically active substance of the present invention was administered to her. The side effects of the anti-cancer agents were potentiated. It is possibly indicated that the combination of the biologically active substance of the present invention with anti-cancer agents is effective.

Clinical Case 5

A female of age 22 was diagnosed as having uterine cancer. Because cancer cells were detected during her pregnancy, the biologically active substance of the present invention was immediately administered. About three months later, the mother delivered a healthy baby, while the mother herself was in a healthy state.

Clinical Case 6

A male of age 20 was diagnosed with a cerebral tumor. His tumor was serious, causing disorders in his speech. The biologically active substance of the present invention was administered to the patient. Four months later, on Jan. 10, 1997, he was recovered to such a state that he could be released from the hospital.

Clinical Case 7

Additionally, 100 cases are now under examination at Tosa Shimizu Hospital in Kochi Prefecture, Japan. It is believed that the biologically active substance of the present invention will be effective generally.

NK activity will now be described below in clinical Cases.

White blood cells include NK cells (natural killer cells) other than B cells, T cells, and macrophages. It has been known that NK cells directly attack cancer cells. The activity is called NK activity. NK activity is represented by the ratio in % of killed cancer cells in number within 3 hours.

For example, NK activity of 55 means that 50 cancer cells among 100 cancer cells were killed in 3 hours. A larger value means higher NK activity. Generally, the NK activity is 55 to 75 in normal subjects and about 20 to 40 in cancer patients. When the NK activity is not less than 55, the NK attack of cancer cells exceeds the proliferation of cancer cells, so that the cancer may possibly be suppressed or reduced. Therefore, the NK activity should be maintained at not less than 55, but due to the current dietary habit of Japanese people, the NK activity is sometimes below 50.

NK activity will now be described below in Clinical cases.

In vitro Test (Test in Tubes)

Figure 3:
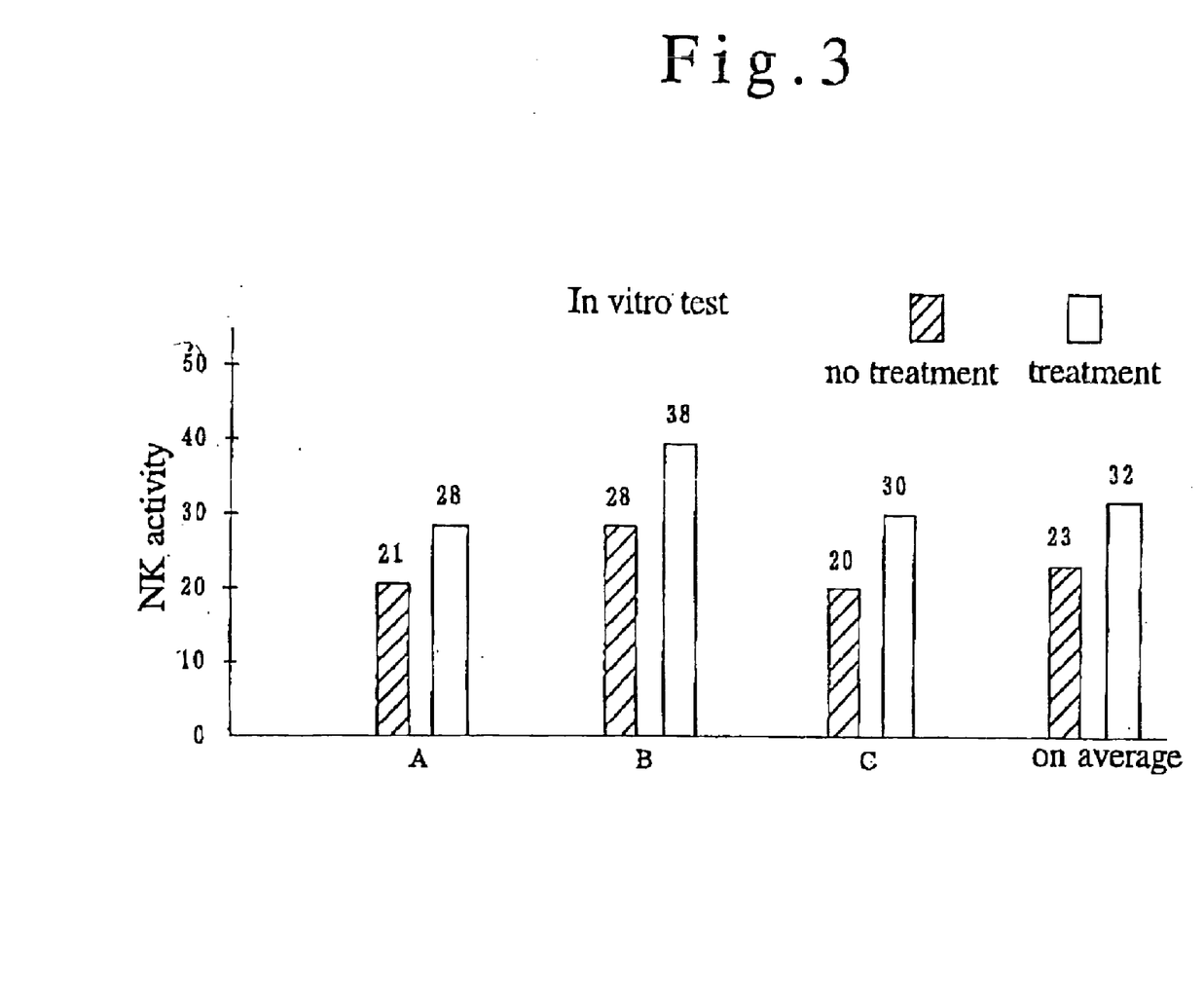
FIG. 3 shows bar graphs of NK activity at in vitro tests.

NK cells were separated from blood of three patients, namely A, B and C. The cells were then subjected to reaction with the biologically active substance of the present invention and were left to stand for 16 hours. Thereafter, the NK activity was assayed. The results were compared with the assay results of NK cells under no action of the biologically active substance of the present invention. The results are shown in FIG. 3. So as to avoid the influence of the concentration of NK cells, the NK cells and cancer cells were tested at three levels of concentrations. The results are shown on average.

In vivo Test (Test in Organisms)

The biologically active substance of the present invention was given to two subjects, namely D and E, at about 50 mg per day for one week. NK cells were collected from the blood, for the assay of the NK activity. The NK activity was assayed in the same manners as described above. The results were compared with the NK activity prior to the administration of the biologically active substance of the present invention.

Figure 4:
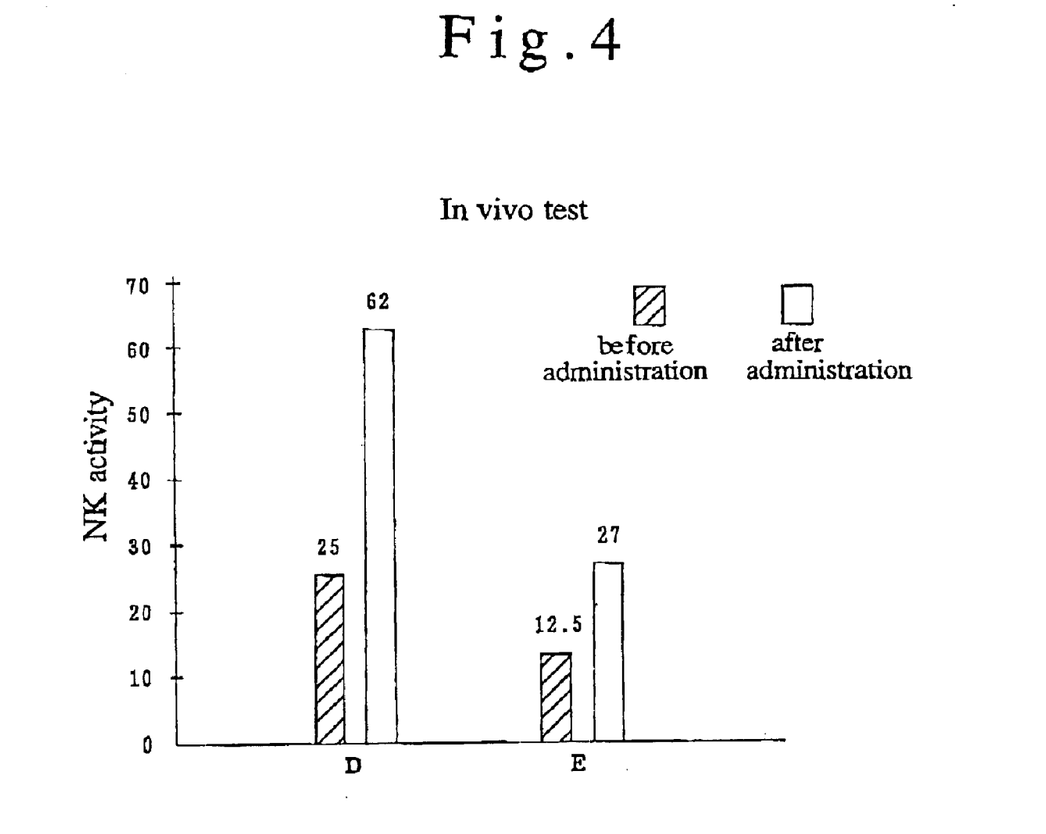
FIG. 4 shows bar grapes of NK activity at in vivo tests.

The results are shown in FIG. 4.

Abbreviated Words (Technical Terms) used in the specification are respectively as follows.

NK cell: natural killer cell
MYA medium: malt yeast agar medium
SMY medium: sugar malt yeast medium
LYM: lymphocyte
MCV: mean corpuscular volume
ALT: alanine aminotransferase
NK activity: natural killer cell activity
B cell: bone cell
T cell: thymus cell
in vitro test: a test executed in a test tube made of glass
in vivo test: a test in the living thing
JAM: reference number of micro-organism used by inventors of their own convenience

What is claimed is:

1. A method for preparing a biologically active substance containing β-glucan as a main effective ingredient comprising the steps of:
   adding an enzyme composition comprising hemicellulase to mycelium of *Agaricus blazei*;
   activating the enzyme composition to decompose hemicellulose of the *Agaricus blazei* by a decomposition reaction;
   stopping the decomposition reaction executed by the enzyme composition by adjusting the pH to not lower than 6.5, optionally from 7.0 to 7.5, to inactivate the enzyme composition; and
   recovering the biologically active substance containing β-glucan.

2. A method for preparing a biologically active substance containing β-glucan as a main effective ingredient comprising the steps of:
   adding an enzyme composition comprising hemicellulase to mycelium of *Agaricus blazei*;
   activating the enzyme composition to decompose hemicellulose of the *Agaricus blazei* by a decomposition reaction;
   stopping the decomposition reaction executed by the enzyme composition by adjusting the pH to not lower than 6.5, optionally from 7.0 to 7.5, and further adjusting the temperature to not lower than 60° C. to inactivate the enzyme composition; and
   recovering the biologically active substance containing β-glucan.

3. The method according to claim 2 wherein the temperature is adjusted to 70 to 85° C.

4. A method for preparing a biologically active substance containing β-glucan as a main effective ingredient comprising the steps of:
   adding an enzyme composition comprising hemicellulase to fruit body of *Agaricus blazei*;
   activating the enzyme composition to decompose hemicellulose of the *Agaricus blazei* by a decomposition reaction;
   stopping the decomposition reaction executed by the enzyme composition by adjusting the pH to not lower than 6.5, optionally from 7.0 to 7.5, to inactivate the enzyme composition; and
   recovering the biologically active substance containing β-glucan.

5. A method for preparing a biologically active substance containing β-glucan as a main effective ingredient comprising the steps of:
   adding an enzyme composition comprising hemicellulase to fruit body of *Agaricus blazei*;
   activating the enzyme composition to decompose hemicellulose of the *Agaricus blazei* by a decomposition reaction;

stopping the decomposition reaction executed by the enzyme composition by adjusting the pH to not lower than 6.5, optionally from 7.0 to 7.5, and further adjusting the temperature to not lower than 60° C. to inactivate the enzyme composition; and recovering the biologically active substance containing β-glucan.

6. The method according to claim 5 wherein the temperature is adjusted to 70 to 85° C.

7. A method for preparing a biologically active substance containing β-glucan as a main effective ingredient comprising the steps of:

adding an enzyme composition comprising hemicellulase to cultured liquid filtered after culturing mycelium of *Agaricus blazei;* activating the enzyme composition to decompose hemicellulose of the *Agaricus blazei* by a decomposition reaction;

stopping the decomposition reaction executed by the enzyme composition by adjusting the pH to not lower than 6.5, optionally from 7.0 to 7.5, to inactivate the enzyme composition; and recovering the biologically active substance containing β-glucan.

8. A method for preparing a biologically active substance containing β-glucan as a main effective ingredient comprising the steps of:

adding an enzyme composition comprising hemicellulase to cultured liquid filtered after culturing mycelium of *Agaricus blazei;* activating the enzyme composition to decompose hemicellulose of the *Agaricus blazei* by a decomposition reaction;

stopping the decomposition reaction executed by the enzyme composition by adjusting the pH to not lower than 6.5, optionally from 7.0 to 7.5, and further adjusting the temperature to not lower than 60° C. to inactivate the enzyme composition; and recovering the biologically active substance containing β-glucan.

9. The method according to claim 8 wherein the temperature is adjusted to 70 to 85° C.

10. The method according to claim 1, wherein the pH is 7.0–7.5.

11. The method according to claim 2, wherein the pH is 7.0–7.5.

12. The method according to claim 4, wherein the pH is 7.0–7.5.

13. The method according to claim 5, wherein the pH is 7.0–7.5.

14. The method according to claim 7, wherein the pH is 7.0–7.5.

15. The method according to claim 8, wherein the pH is 7.0–7.5.

* * * * *